United States Patent
Altmann

(10) Patent No.: US 6,817,714 B2
(45) Date of Patent: Nov. 16, 2004

(54) METHOD AND APPARATUS RELATING TO THE OPTICAL ZONE OF AN OPTICAL ELEMENT

(75) Inventor: Griffith E. Altmann, Webster, NY (US)

(73) Assignee: Bausch and Lomb, Inc., Rochester, NY (US)

(*) Notice: Subject to any disclaimer, the term of this patent is extended or adjusted under 35 U.S.C. 154(b) by 110 days.

(21) Appl. No.: 10/254,382

(22) Filed: Sep. 25, 2002

(65) Prior Publication Data

US 2004/0057010 A1 Mar. 25, 2004

(51) Int. Cl.$^7$ .............................................. G02C 13/00
(52) U.S. Cl. ....................... 351/177; 351/178; 351/219; 369/275.1
(58) Field of Search .................................. 351/177, 178

(56) References Cited

U.S. PATENT DOCUMENTS

2002/0001071 A1 * 1/2002 Nomura et al. ............... 355/52
2002/0008869 A1 * 1/2002 Van der Laan et al. ...... 356/124

FOREIGN PATENT DOCUMENTS

WO   WO 01/89424 A1   11/2001

OTHER PUBLICATIONS

AS "Efficient computation with special functions like the circle polynomial of Zernike", by Riera, et al., *SPIE* 2002 4769–15, 12:45:28, Aug. 1, 2002.

* cited by examiner

Primary Examiner—Scott J. Sugarman
Assistant Examiner—Darryl J. Collins
(74) Attorney, Agent, or Firm—William J. Greener; Craig E. Larson

(57) ABSTRACT

The invention relates to the determination of higher-order aberrations of an optical element over an optical zone that is larger than the typically limited measured zone over which the aberrations are measured. This is accomplished by apparatus, systems, and methods in which, preferably, the Zernike data from an aberration measurement is fit to a conic function. The conic function smoothly and continuously increases or decreases between the measured zone and the optical zone allowing the extrapolated data to accurately determine the aberrations over the optical zone. According to the invention, a plurality of independent conic plus piston sections that vary azimuthally can very accurately describe a wavefront aberration composed of defocus, astigmatism, spherical aberration, secondary astigmatism, and tetrafoil. The description of primary coma and trefoil will not be as good because they vary with the $3^{rd}$ order of the radial component. However, the description error is relatively small. A tilt term can be added to account for the tilt component of the coma and trefoil terms.

18 Claims, 3 Drawing Sheets

METHOD AND APPARATUS RELATING TO THE OPTICAL ZONE OF AN OPTICAL ELEMENT

BACKGROUND OF THE INVENTION

1. Field of the Invention

The invention is generally directed to the field of ophthalmic vision correction, and more specifically to a method, a readable medium, and a system related to determining the optical zone associated with higher-order aberration correction provided by a custom contact lens, a custom IOL, a corneal inlay, or refractive laser surgery.

2. Description of Related Art

Until about the beginning of the last decade, vision correction consisted of approximately determining the lower order aberrations of a person's eyes, namely defocus, cylinder (astigmatism) and the cylinder axis, and prescribing spectacle or contact lenses to approximately correct these aberrations.

More recently, however, the application of wavefront sensor technology (aberrometers) to the field of ophthalmic vision correction has allowed practitioners to accurately measure the higher-order aberrations of optical systems such as the eye. These higher-order aberrations include secondary astigmatism, spherical aberration, coma, trefoil; and others known to those skilled in the art. Moreover, advances in lens design and manufacturing, and laser vision correction methods and apparatus, have made it possible to correct certain of the higher-order aberrations with customized contact lenses, custom IOLs, and photoablative refractive surgery. In many patients, the theoretical limit of visual acuity, 20/8, has been achieved.

When measuring the ocular aberrations of a patient's eye with an aberrometer or like instrument, the diameter of the measured zone is limited by the smaller of either the instrument's aperture or the patient s pupil. In either case, the diameter of the measured zone is very likely to be smaller than the diameter of the optic zone of a contact lens, typically 7–8 mm, or the diameter of a photorefractive ablation zone, typically 5–6 mm, excluding the blend zone. Since many of the higher-order aberrations depend upon the size of the aperture that the light passes through (i.e., a person's pupil), referred to hereinafter as the "optical zone," it is important to know the identity and magnitude of the aberrations over the full optical zone in order to properly correct them with lenses, surgery, or otherwise. The current method for increasing pupil size is to use mydriatic drugs, like 2.5% phenylephrine hydrochloride, which dilate the pupil beyond its natural maximum size. This is undesirable for measuring ocular aberrations because pupil dilation is linked to accommodative mechanisms. Thus, when the pupil is artificially dilated, the crystalline lens may have an unnatural shape and may be decentered and tilted in ways different than during natural viewing. In addition, the pupil itself may be decentered when artificially dilated. This may alter the aberration contribution of the crystalline lens, and the total wavefront aberration may have errors. Cycloplegic drugs, like 1% tropicamide, which paralyze the ocular cilliary muscles may also be used. These drugs are even less desirable because they directly affect the shape of the crystalline lens.

The wavefront aberration over the measured zone is commonly described by Zernike polynomials with a normalization radius set to the half-diameter of the measured zone. Extrapolation of Zernike polynomials beyond their normalization radius is undesirable because Zernike polynomials behave wildly outside their normalization radius. Another possibility is to refit the data with Zemike polynomials having a normalization radius of 4 mm (i.e. 8 mm diameter). Although the Zernike polynomials will be better behaved, there is no reason to believe that the data created between the edges of the measured and optical zone is appropriate. Similar problems are encountered when extrapolation of other types of polynomial expressions are used to describing higher-order aberrations outside of the measurement zone.

In view of these shortcomings, the inventor has recognized a need for the ability to accurately and simply describes the optical aberrations beyond the typically measured zone, and extending over the optical zone of a contact lens or the patient's eye.

SUMMARY OF THE INVENTION

The invention broadly relates to methods and apparatus allowing a simple and accurate determination of higher-order aberrations of an optical clement over an optical zone that is larger than the limited measured zone over which the aberrations typically are measured.

An embodiment of the invention is directed to a machine readable medium that includes an executable instruction directing a suitable machine or device to produce an aberration correcting surface on an optical element. For a custom surface (i.e., non-rotationally symmetric), the instruction directs the making of a meridional shape profile on the optical surface which fits a monotonic function to the aberration data that either increases or decreases smoothly and consistently with increasing radius to a peripheral limit of an optical zone that is larger than a peripheral limit of a measured zone of an optical aberration of the optical element, and extrapolating the aberration data over the optical zone of the element. Most preferably, the function is a conic. In one preferred aspect, the device is a laser suitable for ablating the optical surface of what will typically be a customized contact lens or other ophthalmic lens surface like an IOL or corneal inlay, for example, or a corneal surface. In another preferred aspect, the machine is a numerically controlled lathe such as, e.g, an Optoform 50/Variform® lathe (Precitech, Keene, N.H., USA). In a preferred aspect, the instruction directs the production of a corrective surface by fitting between 24 and 384 separate and independent, uniformly spaced conic functions to determine the full optical surface.

In a related embodiment, a system for making a corrective surface on an optical element includes a device cooperatively engageable with an optical element having a surface intended to be altered to provide an optical aberration correction, preferably a higher-order correction. The device is suitable for altering the surface of the optical element upon an executable instruction and, as such, can receive a readable medium including an executable instruction. The system alternatively includes a control system operatively associated with the device and adapted to receive a readable medium including an executable instruction, and to provide the instruction to the device for execution, and the medium itself The instruction directs the device to produce a meridional shape profile on the optical surface that fits a monotonic function to the aberration data that either increases or decreases smoothly and consistently with increasing radius to a peripheral limit of an optical zone that is larger than a peripheral limit of a measured zone of an optical aberration of the optical element, and extrapolating the aberration data over the optical zone of the element.

In another embodiment, a method for determining (which term includes designing, designating, specifying, or otherwise describing) a corrective optical surface for an optical element over an optical zone having a radius that is greater than that of a measured zone over which an optical aberration of the element has been measured, includes making a higher-order aberration measurement, fitting the aberration data to a function that either increases or decreases smoothly and consistently, and extrapolating the aberration data over the optical zone of the optical surface. In a preferred aspect, the function is a conic. More preferably, between 24 and 384 separate and independent conic functions spaced every 15 degrees to four degrees, respectively, are fit to the measured aberration data to accurately describe the total corrected optical surface.

These and other advantages and objects of the present invention will become more readily apparent from the detailed description of certain embodiments to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF A PREFERRED EMBODIMENT

Figure 1:
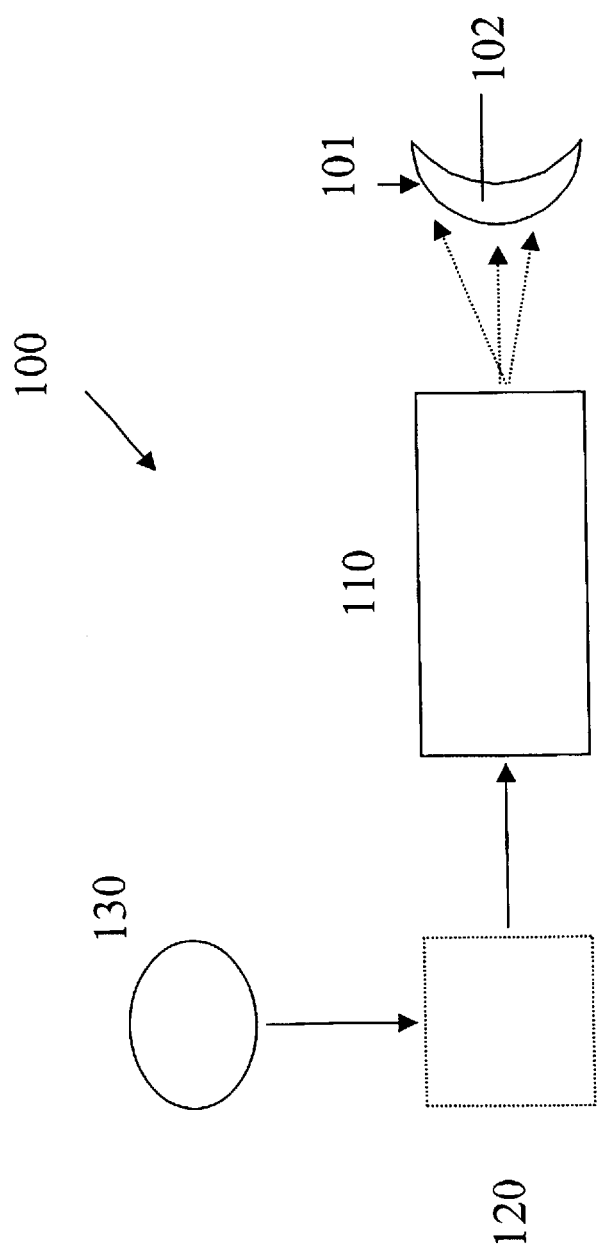
FIG. 1 is a block diagram of a system embodiment of the invention.

FIG. 1 shows a block diagram of a system 100 for creating an aberration correcting surface 101 on an optical element 102, such as, for example, a custom contact lens, a customized IOL, a corneal inlay, or the cornea of an eye. A device 110, preferably a numerically controlled lathe such as, for example, an Optoform 50/Variform® lathe, or a laser such as an ArF excimer laser having a 193 nm output, for example, are suitable for altering the surface 101 of the optical component 102 to create an aberration correcting surface. The device 110 requires an instruction 132 for directing the operation of the device, this instruction being provided in a medium 130 that is readable by the device 110 directly, or alternatively, through a control system 120 shown in dotted lines. It should be understood that the instruction 132 can be encoded software, a minifile, or any other executable form useable by the device 110 and/or the control system 120. The readable medium 130, likewise, will be in a form suitable for carrying the instruction 132 and readable by the control system 120 or the device 110. Accordingly, the medium 130 is preferably a disk, CD, DVD, or other physical media such as a card or smart card, for example; or the medium 130 may be a telecommunications waveguide such as a telephone line or modem link that transmits the instruction in the form of a signal; or, further, the medium may be an electromagnetic transmission such as a carrier wave with an embedded signal instruction.

Regardless of the form, the instruction 132 instructs the device in producing a corrective optical surface having a meridional cross sectional profile defined by $$z_i = (r^2 i)/\{1 + \sqrt{[1-(1+k_i)r^2/R^2]}\} + a_i + B_i r;$$

where for each conic meridian, i,
r = a radial component (mm),
$R_i$ = the vertex radius (mm) of meridian (i),
$k_i$ = the conic constant of meridian (i),
$z_i$ = the sag of meridian (i),
$a_1$ = a piston coefficient (mm) of meridian (i), and
$B_i$ = a radial tilt coefficient (constant) of meridian (i), further wherein the profile extends over an optical zone radius $R_{oz}$ that is greater than a measured aberration zone radius $R_{meas}$. The optical zone $R_{OZ}$ will preferably have a diameter of between about 7 mm and 11 mm, and more preferably of between about 7 mm–8 mm for a custom contact lens, for example, or between about 5 mm–6 mm for a photorefractive ablation zone excluding a blend zone. Most preferably, the function is a conic. The sag profile of a conic is described by its vertex radius and conic constant and either increases or decreases monotonically with increasing radial component.

Figure 2:
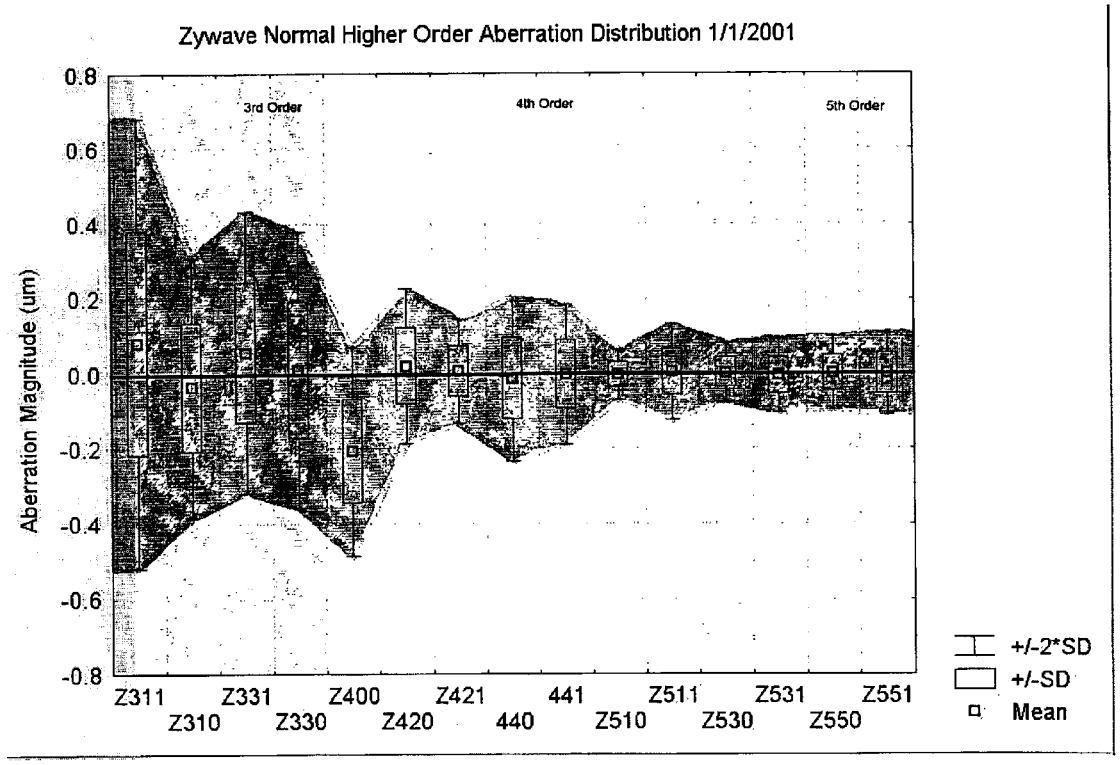
FIG. 2 is a chart showing a population distribution of measured aberrations.

It is known that the normal human eye suffers from spherical aberration, which varies as the $4^{th}$ order of the radial component (i.e. spherical aberration is proportional to $r^4$). Defocus and spherical aberration are correctable with a conic profile, since a conic varies with the $2^{nd}$ order and $4^{th}$ order of the radial component. Moreover, a plurality of independent conic plus piston sections that vary azimuthally can very accurately describe a wavefront aberration composed of defocus, astigmatism, spherical aberration, secondary astigmatism, and tetrafoil. A tilt term is added to account for the tilt component of the coma and trefoil terms. FIG. 2 shows a distribution of measured aberrations among a sample population. It can be seen that defocus ($Z_x$), astigmatism ($Z_x$), and spherical aberration ($Z_x$) represent the dominant aberrations, which are correctable according to the invention.

Figure 3:
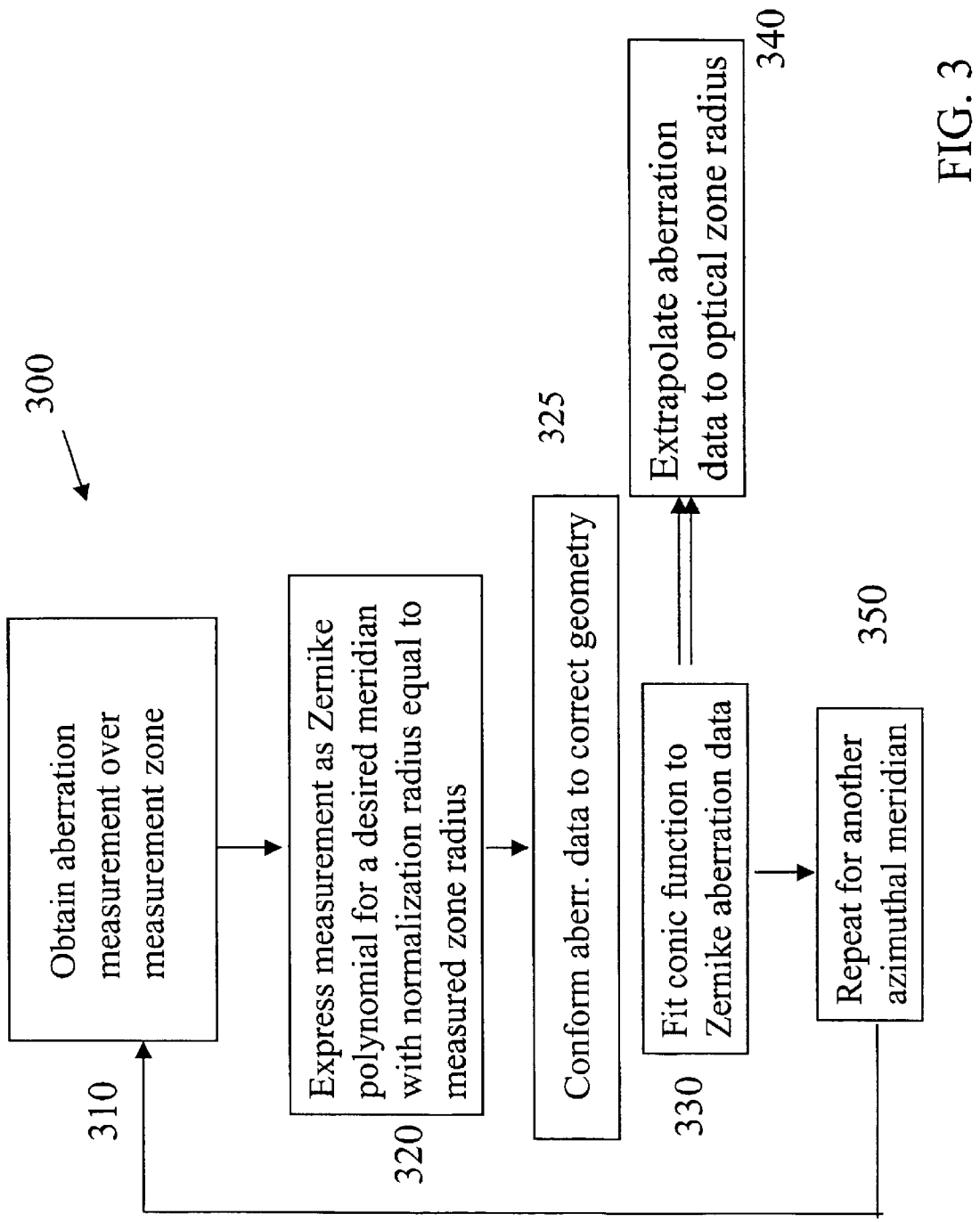
FIG. 3 is a flow process diagram illustrating a design method according to an embodiment of the invention.

FIG. 3 shows a process flow diagram 300 for determining an aberration correcting optical surface for an optical element over an optical zone that is larger than a measured zone of an optical aberration of the element or an optical system including the element. An aberrometer or like instrument used to obtain an aberration measurement provides the measurement over a measurement zone that typically is restricted to less than an 8 mm diameter by a limiting aperture of the device. When the element being measured is an eye, the pupil diameter, which also is usually smaller than 8 mm in diameter, sets the measurement zone size. However, it is desirable to know the optical aberrations, particularly the higher-order aberrations, of the element or the optical system including the element over a larger zone, referred to as the optical zone. In this embodiment of the invention, this is accomplished by obtaining an aberration measurement of the optical element over a measurement zone at step 310; expressing the measurement preferably as a Zernike polynomial having a normalization radius equal to the radius of the measured zone, for a desired meridian at step 320; fitting a conic function to the aberration data at step 330, and extrapolating the aberration data at step 340 to an optical zone radius at the meridian that is larger than the measured zone radius. Preferably, the optical zone will have a diameter of between about 7 mm and 11 mm, and more preferably of between about 7 mm–8 mm for a custom contact lens, for example, or between about 5 mm–6 mm for a photorefractive ablation zone excluding a blend zone. These steps can then be repeated at step 350 for another azimuthal meridian until the entire optical surface has been mapped. Preferably, between 24 and 384 separate and independent fittings are made at equally spaced intervals, for example, 15 degrees and 0.9375 degrees, respectively. Most preferably, each meridional profile will be expressed as $$z_i = (r^2/R_i)/\{1+\sqrt{[1+k_i)r^2/R^2]}\} + a_i + B_i r,$$

where for each conic meridian, i, r=a radial component (mm), $R_i$=the vertex radius (mm) of meridian (i), $k_i$=the conic constant of meridian (i), $z_i$=the sag of meridian (i), $a_i$=a piston coefficient (m m) of meridian (i), and $B_i$=a radial tilt coefficient (constant) of meridian (i), wherein the profile extends over an optical zone radius $R_{OZ}$ that is greater than a measured aberration zone radius $R_{meas}$. Moreover, a plurality of independent conic plus piston sections that vary azimuthally can very accurately describe a wavefront aberration composed of defocus, astigmatism, spherical aberration, secondary astigmatism, and tetrafoil. A tilt term is added to account for the tilt component of the coma and trefoil terms.

The invention is not limited to using a Zernike expression for the aberration information. Other expressions include the Legendre and Taylor polynomials. As reported, some processor intensive calculations are better performed using Taylor polynomials (D. M. Topa, "Computing with Taylor polynomials in lieu of Zernike polynomials", 3rd International Congress of Wavefront Sensing and Aberration-Free Refractive Correction, Interlaken, Switzerland, Feb. 15–17, 2002). Legendre polynomials are orthogonal and are only valid over a normalized range, similar to Zernike polynomials. Taylor polynomials are not orthogonal and do not have a normalization radius.

It should be appreciated by those skilled in the art that prior to fitting the conic profiles according to the invention as described above, wavefront output from an aberrometer may require conformation into corrective surface geometry as shown at step 325 of FIG. 3. This includes, for example, correction for image rotation, wavelength conversion, and power shift as further described below. In an exemplary embodiment, an ocular aberrometer such as the Zywave® wavefront analyzer (Bausch & Lomb, Incorporated, Rochester, N.Y.) incorporating a Hartmann-Shack wavefront sensor (HSWFS), measures the wavefront aberration exiting an individual patient's eye at the eye's entrance pupil plane. This is accomplished by injecting a narrow beam of infra-red laser radiation into the patient's eye along the patient's visual axis. The wavelength of the measurement beam is 780 nm. The laser energy diffusely reflects off the patient's fovea and passes back through the eye completely filling the patient's physical pupil. Aberrometer optics relay the image of the physical pupil, defined as the entrance pupil, onto the HSWFS, which samples the wavefront at known intervals. A computer then calculates a complete mathematical description of the patient's exiting wavefront aberration in the form of Zernike polynomials as per Born & Wolf, *Principles of Optics*, 6th Edition, Cambridge University Press (1980). This wavefront aberration can be used to design a custom-correction solution for the patient via an ophthalmic lens or refractive surgery.

Data provided by the Zywave aberrometer includes a set of 18 Zernike coefficients ($T_3$ through $T_{20}$) measured in microns; a normalization radius value ($R_N$) expressed in mm; and equivalent sphere power ($S_E$).

Image Rotation

In the Zywave device the wavefront aberration at the patient's entrance pupil is rotated 180 degrees before it reaches the HSWFS. Thus the Zernike coefficients must be modified to account for this rotation by multiplying all coefficients with odd-theta dependence by (−) 1. Those coefficients with no theta-dependence or even-theta dependence are not modified.

Wavelength Conversion

Light at 780 nm focuses deeper into the eye than does light at 555 nm which is the peak wavelength of normal viewing. Thus wavefront measurement at 780 nm provides an erroneous correction on the order of +0.45D from the actual correction. The measured power, B, can be expressed as:

$$B = S_E - 0.45$$

where $S_E = [R_N^2 + (2\sqrt{(3)}T_3)^2]/(2 \cdot 2\sqrt{(3)} T_3)$.

Since defocus is primarily defined by the fourth Zernike term, $T_3$ must also be modified to account for this chromatic aberration.

Power Shift

The aberration coefficients must be transformed from the measurement plane to the correction plane (i.e., from the pupil plane to the corneal plane or to the appropriate lens plane). For example, the entrance pupil (measurement plane) of a typical human eye is located substantially 3.1 mm from the anterior surface of the cornea into the eye. A typical custom contact lens has a center thickness of 0.16 mm. Thus, the correction is located 3.26 mm away from the entrance pupil. This distance will cause a slight power shift between measured power error and the correcting power. The shift is expressed in the following equation, where B is the measured power and C is the correcting power located 3.26 mm away from the measurement plane:

$$C = B - 0.00326 \, B^2.$$

Since defocus is primarily defined by the fourth Zernike term, it should also be modified to account for a known power shift. Again, $T_3$ must be modified to account for this power shift.

In an exemplary embodiment, measured aberration data from a patient with severe aberrations was taken over a 7.1-mm pupil. The first 15 standard Zernike terms with a normalization radius of 3.55 mm were used to describe the patient's wavefront aberration. The Zernike coefficients are listed in Table 1.

TABLE 1

| Zernike Term | Coefficient (microns) | Term Description |
|---|---|---|
| Z100 | 0 | Piston |
| Z110 | 0 | |
| Z111 | 0 | Tilt |
| Z200 | −4.442 | Defocus |
| Z221 | −1.195 | |
| Z220 | 5.305 | Primary Astigmatism |
| Z311 | 0.593 | |
| Z310 | 0.491 | Primary coma |
| Z331 | −0.529 | |
| Z330 | 0.435 | Trefoil |
| Z400 | −0.190 | Primary Spherical Aberration |
| Z420 | 0.349 | |
| Z421 | 0.357 | Secondary Astigmatism |
| Z440 | −0.319 | |
| Z441 | −0.260 | Tetrafoil |

Separate and independent conic profiles were fit to the wavefront aberration along 24 meridians spaced 15 degrees apart over a 5 mm central zone using a least-squares routine. The fits along the meridians showed worst case P-V and RMS errors of 0.129 µm and 0.032 µm, respectively. The quality of these fits was then examined (taken over a 5 mm central zone) with respect to all of the data over the 7.1-mm pupil. As expected the quality of the fits decreased, but by reasonable amounts. In the worst case, the P-V and RMS errors were 1.4331 µm and 0.359 µm, respectively, and these errors occurred at the outer edge of the 7.1 mm pupil. It is likely that better fitting routines can be developed to improve the quality of this method.

While various advantageous embodiments have been chosen to illustrate the invention, it will be understood by those skilled in the art that changes and modifications can be made therein without departing from the scope of the invention as defined in the appended claims.

I claim:

1. A method for determining an aberration correcting optical surface for an optical element over an optical zone that is larger than a measured zone of an optical aberration of the system, comprising:

obtaining an aberration data over the measured zone;

expressing the measured aberration in a mathematical form;

conforming the aberration data into a corrective surface geometry;

fitting a monotonic function to the aberration data that either increases or decreases smoothly and consistently and extrapolating the aberration data over the optical zone of the system.

2. The method of claim 1, wherein the aberration data comprises at least $4^{th}$ order or higher-order data as defined by a Zernike polynomial representation of the aberration data.

3. The method of claim 1, wherein fitting a function to the aberration data comprises fitting a conic function to the data.

4. The method of claim 3, comprising fitting a plurality of separate and independent conic functions over a respective plurality of meridians to describe the corrective optical surface.

5. The method of claim 4, comprising fitting between 24 and 90 equally spaced meridians over a 360 degree field to describe the corrective optical surface.

6. The method of claim 1, wherein the optical zone has a diameter of between about 7 mm to 11 mm.

7. The method of claim 6, wherein the optical zone has a diameter of between about 7 mm to 8 mm for a contact lens.

8. The method of claim 6, wherein the optical zone has a diameter of between about 5 mm to 7 mm for a corneal ablation.

9. The method of claim 1, comprising expressing the measured aberration in the form of one of a Zernike polynomial, a Legendre polynomial, and a Taylor polynomial.

10. The method of claim 9, comprising utilizing a normalization radius for the Zernike expression and the Legendre expression, wherein the normalization radius is set to a radius value of the measured zone.

11. A customized contact lens made according to the method of claim 1.

12. A customized IOL made according to the method of claim 1.

13. A cornea ablation designed according to the method of claim 1.

14. A customized corneal inlay according to the method of claim 1.

15. A machine readable medium storing an executable instruction for altering a surface of an aberrated optical system to create a corrective optical surface, wherein the instruction instructs the machine in producing a corrective optical surface having a meridional cross sectional profile defined by $$z_i = (r^2/R_i)/\{1+\sqrt{[1-(1+k_i)r^2/R^2]}\} + a_i + B_i r,$$

where for each conic meridian, i, r = a radial component (mm), $R_i$ = the vertex radius (mm) of meridian (i), $k_i$ = the conic constant of meridian (i), $z_i$ = the sag of meridian (i), $a_i$ = a piston coefficient (mm) of meridian (i), and $B_i$ = a radial tilt coefficient (constant) of meridian (i), further wherein the profile extends over an optical zone radius $R_{OZ}$ that is greater than a measured aberration zone radius $R_{meas}$.

16. The machine readable medium of claim 15, comprising a plurality of separate and independent meridional cross sectional profiles defining the corrective optical surface.

17. The machine readable medium of claim 16, comprising between 24 to 90 separate and independent meridional cross sectional profiles over a 360 degree field defining the corrective optical surface.

18. A system for making an aberration correcting surface in an optical element, comprising:

a device cooperatively engageable with the optical element which has a surface intended to be altered to provide the optical aberration correction, said device being suitable for altering the surface of the optical element upon an executable instruction;

a control system operatively associated with the device and adapted to receive a medium including the instruction and to provide the institution to the device for execution; and a medium including the executable instruction suitable for reading by the control system and for execution of the instruction by the device, wherein the instruction instructs the device to make a corrective optical surface having a meridional cross sectional profile defined by $$z_i = (r^2/R_i)/\{1+\sqrt{[1-(1+k_i)r^2/R^2]}\} + a_i + B_i r,$$

where for each conic meridian, i,
   r = a radial component (mm),
   $R_i$ = the vertex radius (mm) of meridian (i),
   $k_i$ = the conic constant of meridian (i),
   $z_i$ = the sag of meridian (i),
   $a_i$ = a piston coefficient (mm) of meridian (i), and
   $B_i$ = a radial tilt coefficient (constant) of meridian (i),
   further wherein the profile extends over an optical zone radius $R_{OZ}$ that is greater than a measured aberration zone radius $R_{meas}$.

* * * * *

UNITED STATES PATENT AND TRADEMARK OFFICE
CERTIFICATE OF CORRECTION

PATENT NO. : 6,817,714 B2
DATED : November 16, 2004
INVENTOR(S) : Griffith E. Altmann It is certified that error appears in the above-identified patent and that said Letters Patent is hereby corrected as shown below:

Column 7,
Lines 52 and 56, replace "Zemike" with -- Zernike --

Column 8,
Line 1, replace "cornea" with -- corneal --
Line 41, replace "institution" with -- instruction --

Signed and Sealed this

Nineteenth Day of July, 2005

JON W. DUDAS
*Director of the United States Patent and Trademark Office*